(12) United States Patent
Wandke et al.

(10) Patent No.: US 11,490,500 B2
(45) Date of Patent: Nov. 1, 2022

(54) ELECTRODE ARRAY FOR A DIELECTRICALLY IMPEDED PLASMA TREATMENT

(71) Applicant: CINOGY GMBH, Duderstadt (DE)

(72) Inventors: Dirk Wandke, Heiligenstadt (DE); Mirko Hahnl, Berlingerode (DE); Karl-Otto Storck, Duderstadt (DE); Leonhard Trutwig, Duderstadt/Gerblingerode (DE); Melanie Ricke, Katlenburg-Lindau (DE)

(73) Assignee: CINOGY GMBH, Duderstadt (DE)

( * ) Notice: Subject to any disclaimer, the term of this patent is extended or adjusted under 35 U.S.C. 154(b) by 465 days.

(21) Appl. No.: 16/633,439

(22) PCT Filed: Jul. 23, 2018

(86) PCT No.: PCT/EP2018/069929
§ 371 (c)(1),
(2) Date: Jan. 23, 2020

(87) PCT Pub. No.: WO2019/020569
PCT Pub. Date: Jan. 31, 2019

(65) Prior Publication Data
US 2020/0221564 A1    Jul. 9, 2020

(30) Foreign Application Priority Data
Jul. 25, 2017   (DE) .................... 10 2017 116 800.1

(51) Int. Cl.
| | | |
|---|---|---|
| H05H 1/24 | (2006.01) | |
| A61L 2/00 | (2006.01) | |
| A61L 2/26 | (2006.01) | |
| A61N 1/04 | (2006.01) | |
| A61N 1/44 | (2006.01) | |

(52) U.S. Cl.
CPC .......... *H05H 1/2406* (2013.01); *A61L 2/0011* (2013.01); *A61L 2/26* (2013.01); *A61N 1/0476* (2013.01); *A61N 1/44* (2013.01); *A61L 2202/11* (2013.01); *H05H 1/2418* (2021.05)

(58) Field of Classification Search
CPC ...... A61L 2/0011; A61L 2/26; A61L 2202/11; H05H 1/2406; A61N 1/44; A61N 1/0476
See application file for complete search history.

(56) References Cited

U.S. PATENT DOCUMENTS

2013/0345620 A1    12/2013  Zemel et al.

FOREIGN PATENT DOCUMENTS

| | | |
|---|---|---|
| CN | 106668897 A | 5/2017 |
| DE | 102008030913 A1 | 1/2010 |
| DE | 102009060627 A1 | 6/2011 |
| DE | 102009060627 B4 | 6/2014 |
| DE | 102013019057 A1 | 5/2015 |
| DE | 102014013716 A1 | 3/2016 |
| DE | 102014220488 A1 | 4/2016 |
| DE | 102015117715 A1 | 4/2017 |
| KR | 101407672 B1 | 6/2014 |
| WO | 2007/011865 A2 | 1/2007 |

*Primary Examiner* — Sean E Conley
(74) *Attorney, Agent, or Firm* — WCF IP

(57) ABSTRACT

The invention relates to an electrode array for a dielectrically impeded plasma treatment of a surface of a body, comprising at least one flexible flat electrode (1) and one dielectric (2) consisting of a flat flexible first material which protects the electrode (1) from the surface to be treated, with a layer (3) impeding a direct current flow. The dielectric (2) can lie on the surface to be treated, above a structure (4) with projections (7), air spaces (5) being formed between the projections (7) for the creation of the plasma, which have a side open towards the surface to be treated, and a bottom-side closure as a result of the layer (3) impeding the direct current flow. The structure (4) comprises a plurality of spacer elements (6) consisting of a second material that has less flexibility than the first material, and the projections (7) of the structure (4) are partially or completely formed by the spacer elements (6).

16 Claims, 8 Drawing Sheets

Figure 1:
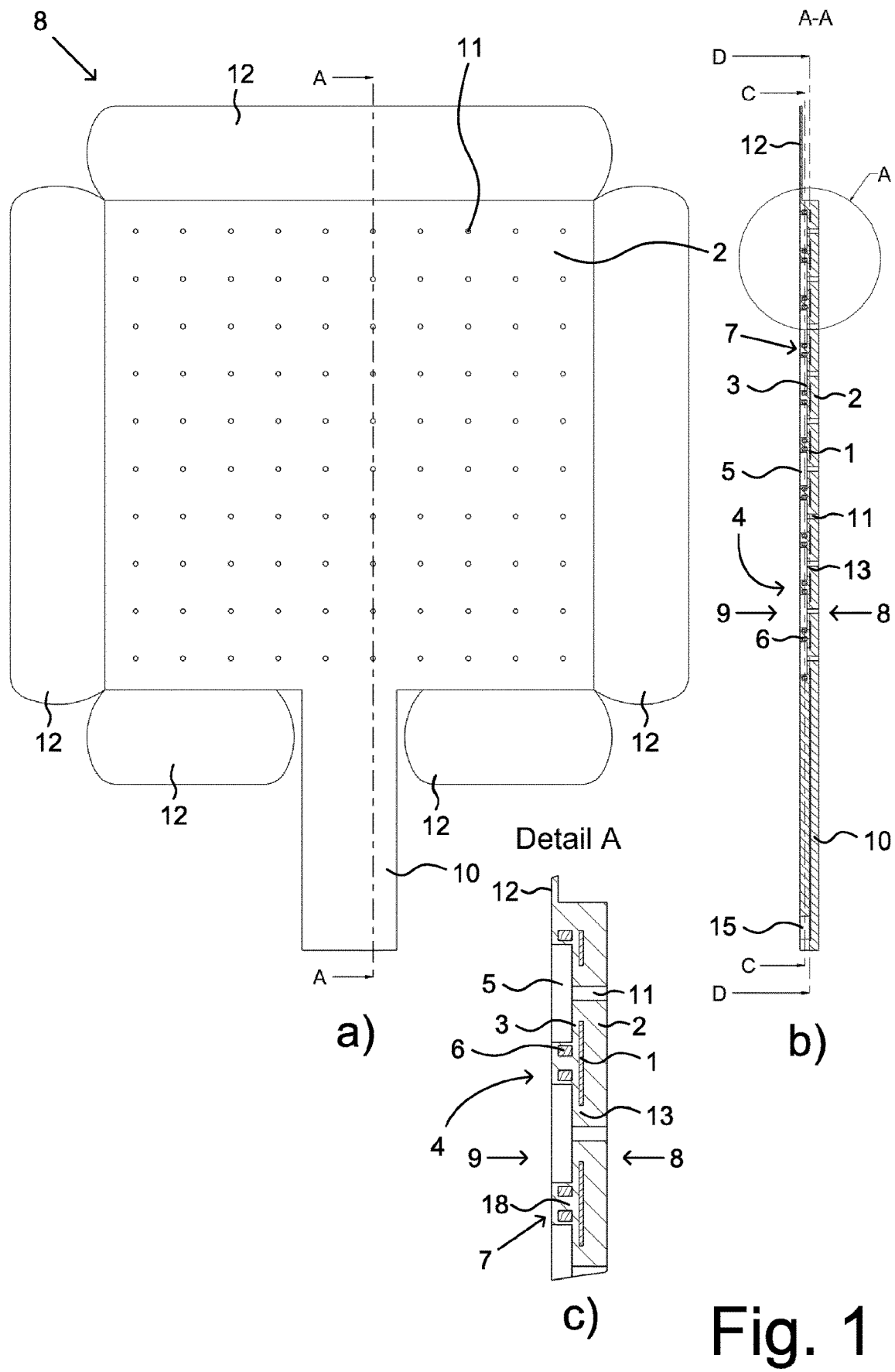

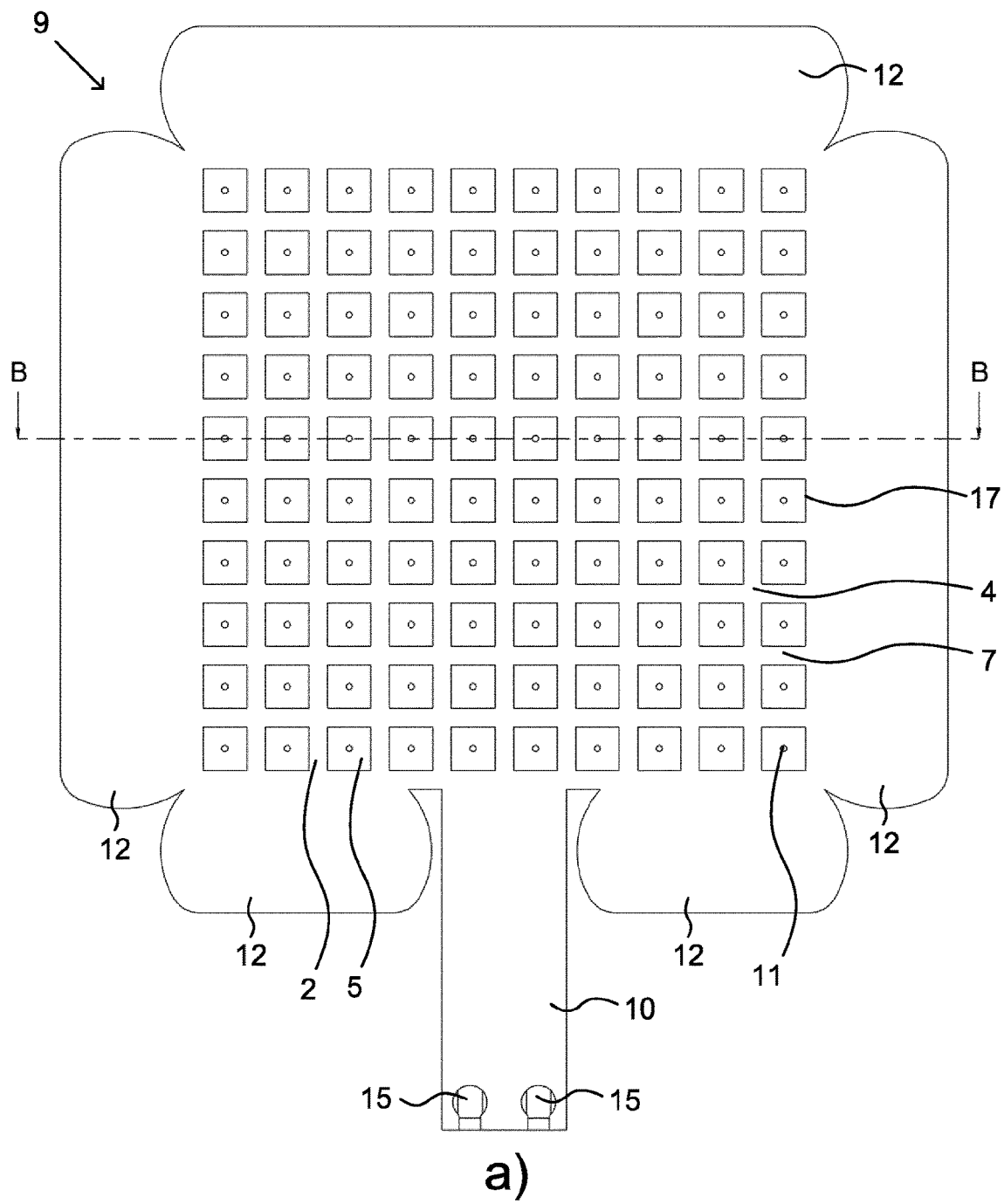
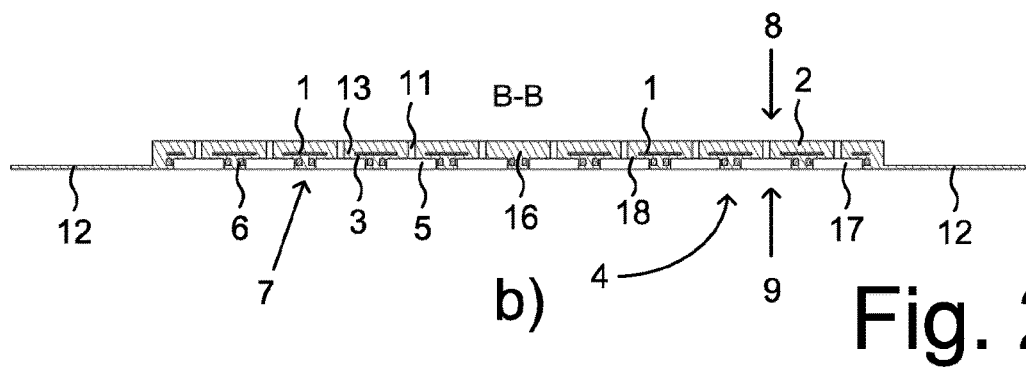
Fig. 2

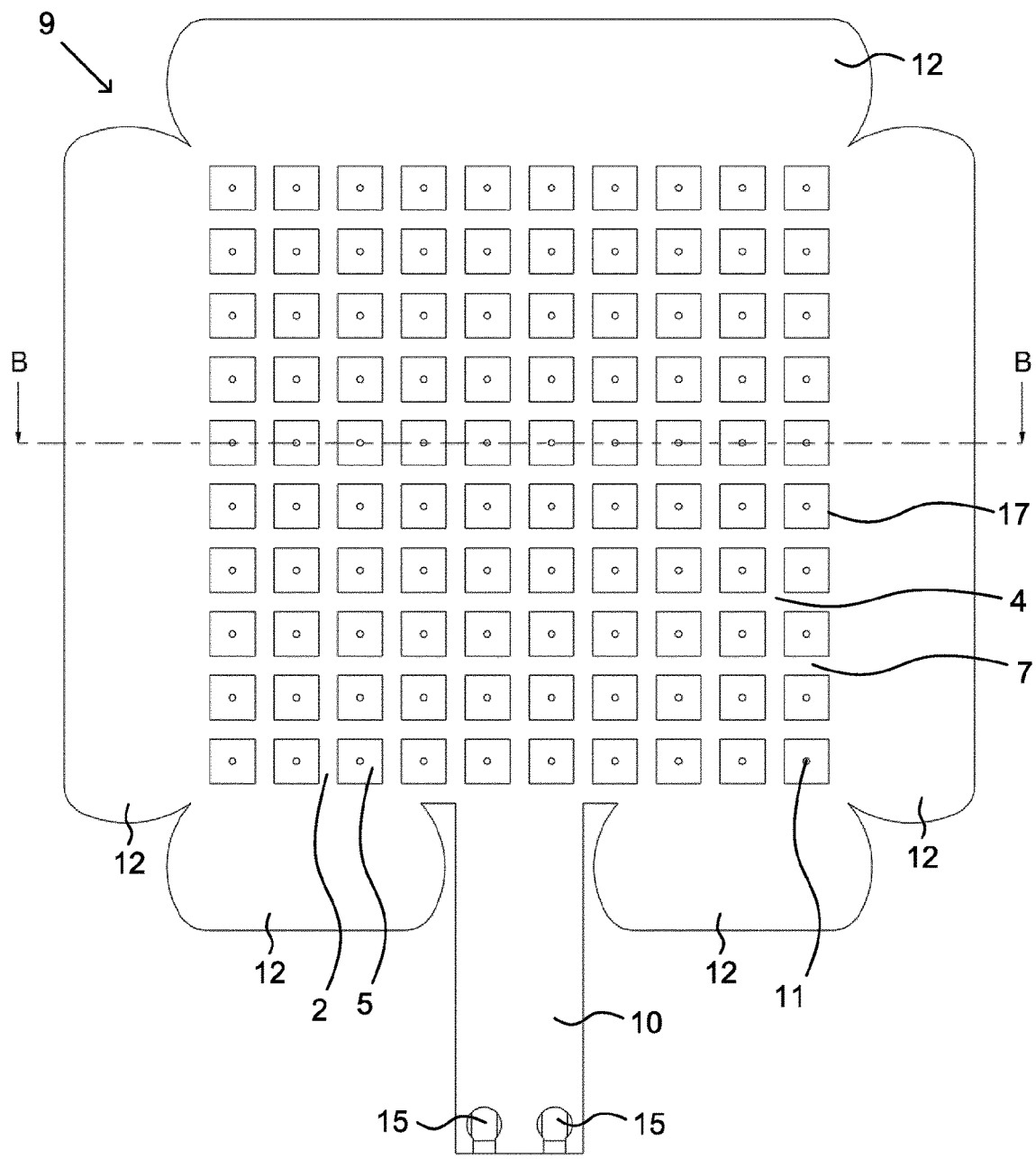
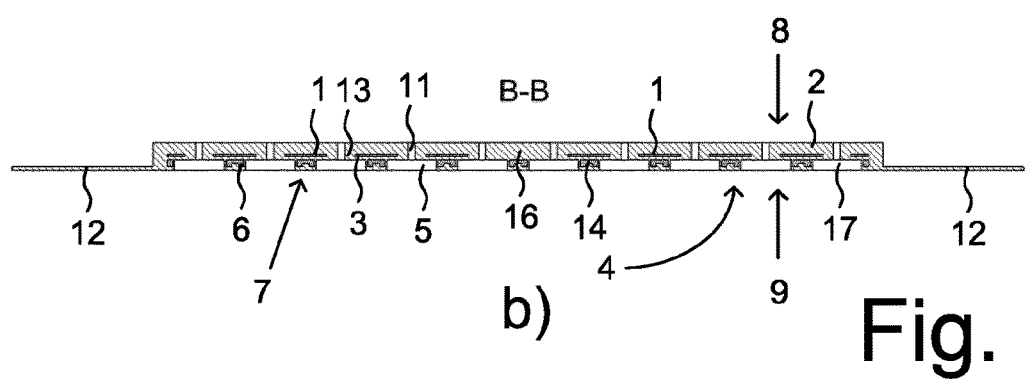
Fig. 5

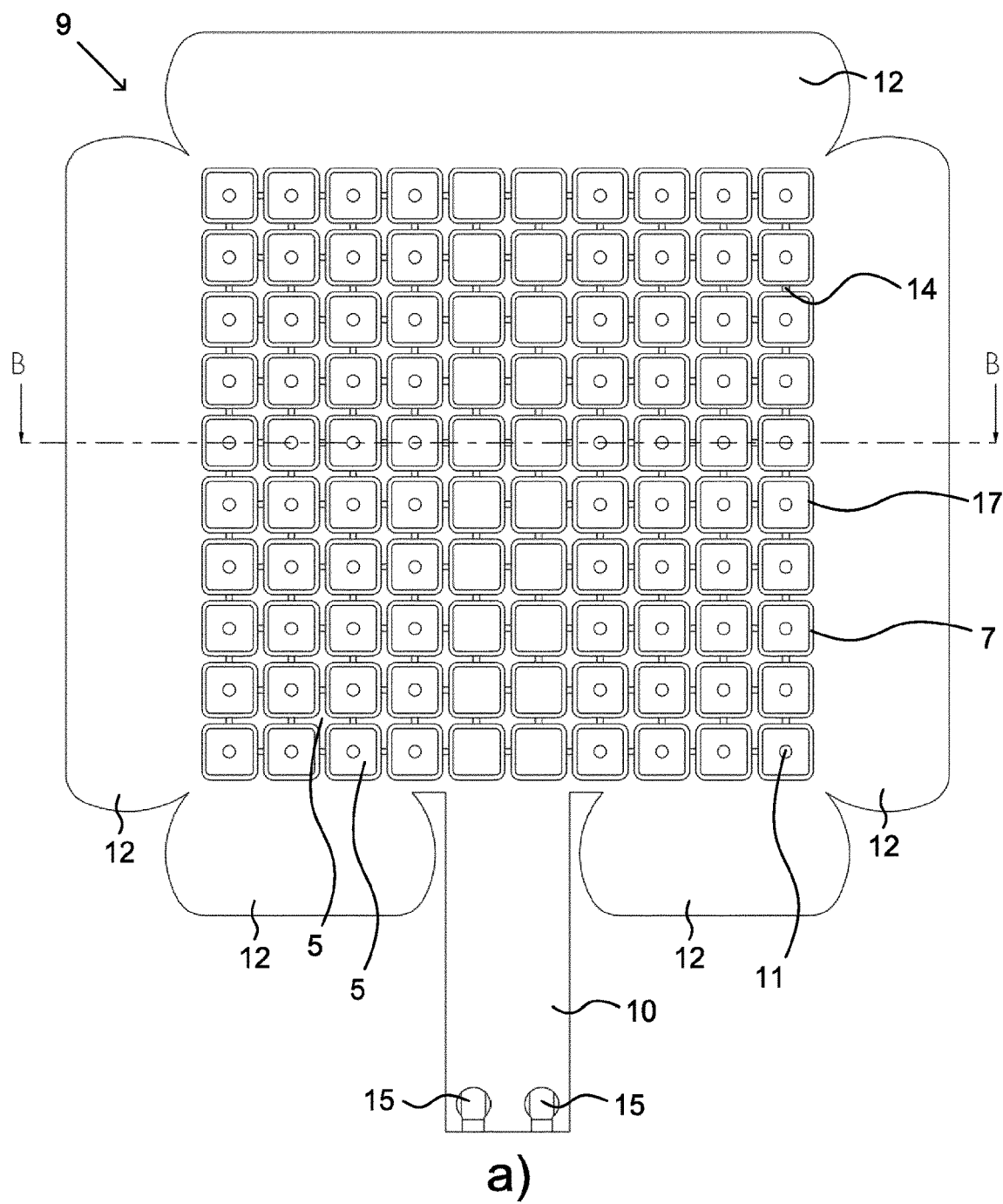
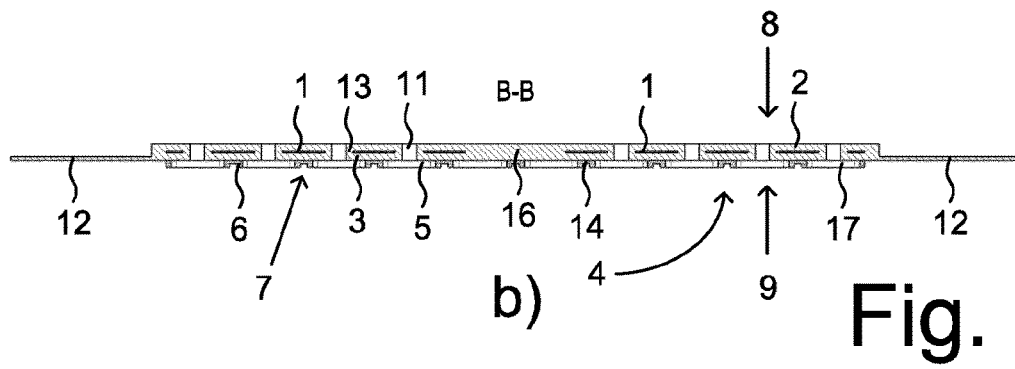
Fig. 8

ELECTRODE ARRAY FOR A DIELECTRICALLY IMPEDED PLASMA TREATMENT

The invention relates to an electrode arrangement for a dielectric barrier plasma treatment of a surface of a body, having at least one flexible planar electrode and a dielectric material made of a planar flexible first material, which shields the electrode from the surface to be treated using a layer preventing a direct current flow, wherein the dielectric material can rest on the surface to be treated via a structure having projections, wherein air spaces for the formation of the plasma are formed between the projections, which comprise a side open toward the surface to be treated and a bottom-side termination by the layer of the dielectric material preventing the direct current flow.

The at least one electrode of the electrode arrangement is connectable to a high voltage required for the plasma generation, which is preferably used as an AC voltage.

The electrode arrangement can in particular advantageously be configured for the surface of the body to be treated to be used as a counter electrode. For this purpose, the body has to be an electrically conductive body, for example, a human or animal body, the skin surface of which is to be treated, or another electrically conductive body.

It is possible for this purpose, for example, to use only a single electrode for generating the plasma and to use the surface or the body, respectively, as the counter electrode (ground). In this way, a large treatment depth within the body is advantageously achieved.

It is furthermore possible, for example, to provide at least two electrodes in the electrode arrangement, to which the same high-voltage potential is applied, so that the surface to be treated on which the electrode arrangement rests functions as the counter electrode for the plasma formation. Alternatively, it is possible, for example, to supply the two electrodes with the AC high voltage in counter phase, wherein the surface to be treated again functions as the counter electrode.

Alternatively, however, it is also possible, for example, to use the at least two electrodes as the electrode and counter electrode, so that the plasma results between the electrodes and can be active in the body as a surface plasma. In this way, however, with a normal energy introduction, only low treatment depths in the body region are enabled.

"Air spaces" are understood in the scope of this application as empty spaces, which are typically filled with air, but can also be filled with a suitable gas for specific applications to form special plasmas.

For an electrode arrangement of the type mentioned at the outset, it is essential that the dielectric material forms a continuous layer, using which the electrode is shielded from the surface to be treated. This layer prevents a direct or galvanic current flow between the electrode and the surface to be treated and is a layer preventing a direct current flow in the meaning of this application.

An electrode arrangement of the type mentioned at the outset is known from DE 10 2009 060 627 B4. Its structure enables the electrode arrangement to also be laid on irregularly bulging surfaces to carry out a plasma treatment. To be able to form the air spaces required for the formation of a plasma between the surface to be treated and the layer of the dielectric material preventing a direct current flow, it is provided that the dielectric material is provided on its side facing toward the surface to be treated with a structure which comprises projections. The structure consists, for example, of protruding nubs, which form air-permeable intermediate spaces.

A further electrode arrangement of the type mentioned at the outset is known from DE 10 2015 117 715 A1. This electrode arrangement is also formed having a structure, so that a plasma can result when the electrode arrangement rests on the surface. The structure is a grid structure made of adjoining walls in this case, which delimit numerous chambers forming the air spaces, which comprise a bottom-side termination by the layer of the dielectric material preventing the direct current flow and a side open toward the surface to be treated. The chambers can have, for example, a square, round, oval, or polygonal cross section.

The known electrode arrangements have proven themselves per se and are also suitable in particular for the treatment of the skin surface of a human or animal body. Due to the plasma treatment, therapeutic or cosmetic active ingredients can be absorbed in an improved manner, so that the plasma treatment reinforces the desired therapeutic or cosmetic effect. In addition, the plasma treatment ensures an effective bacteria reduction, since it destroys microorganisms and in particular exerts a bactericidal and fungicidal effect on the skin. Furthermore, the plasma treatment results in an increase of the microcirculation in the tissue.

In order that such a treatment is also possible on irregularly three-dimensionally formed surfaces, both the electrode and also the dielectric material and the structure with which the electrode arrangement rests on the surface to be treated have to be formed flexibly. To achieve the best possible adaptation of the electrode arrangement to the surface to be treated, it is desirable for the components of the electrode arrangement and in particular the dielectric material to consist of the most flexible possible material. This moreover offers the advantages during the treatment of human or animal bodies that the electrode arrangement can be worn particularly comfortably and pleasantly on the body.

At the same time, however, it has to be ensured that a predetermined distance is maintained between the surface to be treated and the layer of the dielectric material preventing a direct current flow, in order to ensure the desired formation of the plasma in this intermediate space and thus an effective plasma treatment. In the electrode arrangements known from the prior art, it thus has to be ensured that the air spaces formed by the structure and the projections thereof have a predetermined size and in particular a predetermined height during the treatment.

In the electrode arrangements known from the prior art, physical limits are placed on the selection of the flexible material for the electrode arrangement and in particular for the dielectric material of the electrode arrangement by this requirement. If a material is selected for this purpose which has an excessively high flexibility, the predetermined height of the air spaces and thus the predetermined distance between the surface to be treated and the layer of the dielectric material preventing a direct current flow thus can no longer be ensured. This is because the projections of the structure forming the air spaces do not have the required rigidity in this case and deform to an undesired extent during the treatment. The effectiveness of the plasma treatment is thus reduced or an effective plasma treatment is even prevented entirely.

The present invention is therefore based on the stated problem of improving the proven previously known electrode arrangements while maintaining the advantages thereof in such a manner that they adapt themselves in the shape thereof still better to the surface to be treated and enable effective plasma treatment at the same time.

To achieve this object, an electrode arrangement of the type mentioned at the outset is characterized according to the invention in that the structure comprises a plurality of spacer elements made of a second material, the flexibility of which is less than the flexibility of the first material, wherein the projections of the structure are partially or completely formed by the spacer elements.

The spacer elements advantageously ensure a defined distance between the surface to be treated and the layer of the dielectric material preventing a direct current flow. For this purpose, the spacer elements are manufactured from a second material, the flexibility of which is less than the flexibility of the first material, from which the dielectric material of the electrode arrangement is manufactured. In this manner, the electrode arrangement according to the invention enables the dielectric material thereof to be able to be manufactured from a particularly flexible material, which is not usable in the previously known electrode arrangements for the above-explained reasons, to achieve an improved adaptation of the electrode arrangement to the surface to be treated while maintaining the required distance between the surface to be treated and the layer preventing a direct current flow.

A lesser flexibility of the material can be achieved, for example, in that a material is used which has a greater hardness, in particular a greater Shore hardness. A lesser flexibility of the material can also be achieved in that an elastic material having a lesser elasticity is used. The elasticity of the material can be quantified, for example, by its modulus of elasticity and/or its elasticity tensor.

Suitable materials for manufacturing the flexible dielectric material are, for example, flexible silicones, in particular silicone rubbers.

Using the electrode arrangement according to the invention, it is possible, for example, to manufacture the dielectric material of the electrode arrangement from a flexible silicone having a Shore hardness which is less than the lowest Shore hardness of the silicones usable for manufacturing the previously known electrode arrangements. It is possible, for example, to use a silicone having a hardness between 10 Shore and 40 Shore, preferably between 15 and 25 Shore, in particular 20 Shore, for manufacturing the dielectric material. The Shore hardnesses specified in the present application refer to Shore hardnesses according to Shore A Due to the spacer elements of the electrode arrangement according to the invention, an undesired deformation of the projections of the structure can advantageously be avoided during the treatment and maintaining the required distance between the surface to be treated and the continuous layer of the dielectric material preventing the direct current flow from the electrode can thus be ensured. The height of the spacer elements essentially defines the distance here between the surface to be treated and the layer of the dielectric material preventing the direct current flow and thus the height of the air spaces for the formation of the plasma. The height of the spacer elements can advantageously be, for example, between 0.05 mm and 3.0 mm for this purpose.

It is advantageously possible, for example, to manufacture the spacer elements from a stable plastic, which has a lesser flexibility than the material used for the dielectric material, wherein the latter can be, for example, a flexible silicone. It is advantageously also possible, for example, to manufacture both the dielectric material and also the spacer elements of the electrode arrangement according to the invention from a flexible silicone of the above-mentioned type, wherein a silicone having a greater Shore hardness is used for the spacer elements than for the dielectric material. The material used for the spacer elements is fundamentally arbitrary, however, it only has to have a lesser flexibility than the material of the dielectric material.

The projections of the structure can be formed completely by the spacer elements. In this case, the projections consist solely of the spacer elements. However, the projections of the structure can also be formed only partially by the spacer elements. In this case, the spacer elements are namely components of the projections, but the projections also have one or more other components in addition to the spacer elements.

Due to the electrode arrangement according to the invention, the structure can advantageously have a significantly higher flexibility in the area than in the height. In particular, the structure—and thus the electrode arrangement—can advantageously have a low bending rigidity and/or a low torsional rigidity in order to be able to adapt its shape well to the surface to be treated, while the structure at the same time has a large elongation rigidity, i.e., a high level of stability, in relation to forces which act essentially perpendicularly in relation to the surface to be treated, so that it can be ensured that the air spaces are maintained.

In one advantageous refinement of the invention, the spacer elements are connected to one another via connecting sections, which have a lower bending rigidity and/or a lower torsional rigidity than the spacer elements.

The connecting sections can advantageously in particular be connecting sections made of the first material or a third material, the flexibility of which is greater than the flexibility of the second material. In this case, the lesser rigidity of the connecting sections in comparison to the spacer elements is achieved by the greater flexibility of the material of the connecting sections in comparison to the material of the spacer elements.

Alternatively or additionally thereto, the shape of the connecting sections can be formed so that the connecting sections have a lesser rigidity than the spacer elements. The connecting sections can be formed particularly thin or narrow between the spacer elements in comparison to the spacer elements, in particular can have a lesser width and/or a lesser height than the spacer elements.

The connecting sections between the spacer elements can be formed, for example, by the dielectric material of the electrode arrangement, in particular by the layer of the dielectric material preventing a direct current flow. The spacer elements can be connected for this purpose, for example, to the side of the dielectric material facing toward the surface to be treated, in particular to the side of the layer of the dielectric material preventing a direct current flow facing toward the surface to be treated. Since the first material of the dielectric material has a greater flexibility than the second material of the spacer elements, the connecting sections can have a lesser stiffness than the spacer elements particularly simply in this way.

In a further advantageous refinement of the invention, it is provided that the spacer elements are connected to one another by connecting webs and form a spacer grid in this manner.

The shape of the connecting webs is advantageously formed so that the connecting webs have a lesser rigidity than the spacer elements. For this purpose, the connecting webs between the spacer elements can be formed in particular as thin and/or narrow in comparison to the spacer elements. For this purpose, the connecting webs can in particular have a lesser width and/or a lesser height than the spacer elements.

The spacer grid can thus advantageously have a significantly greater flexibility in the area than in the height. In particular, the spacer grid can advantageously have a low bending rigidity and/or a low torsional rigidity in order to be able to adapt its shape well to the surface to be treated, while the spacer grid at the same time has a high elongation rigidity in relation to forces which act essentially perpendicularly to the surface to be treated, i.e., is comparatively stable in relation to these forces, so that it can be ensured the air spaces are maintained.

The connecting webs of the spacer grid can advantageously consist of the same material as the spacer elements themselves, i.e., of the second material.

Alternatively thereto, however, the connecting webs can also consist of a different material. The material of the connecting webs can in particular be a material, the flexibility of which is greater than the flexibility of the material of the spacer elements. The rigidity of the connecting webs can thus advantageously be further reduced.

Such an embodiment of the electrode arrangement according to the invention, in which the spacer elements form a spacer grid by being connected to one another by connecting webs, offers the advantage according to the invention that the stability of the structure and its projections and thus the air spaces formed between the projections can be improved.

In a further advantageous refinement of the invention, it is provided that the spacer grid is integrally formed. This offers the advantage that the spacer grid can be manufactured particularly simply and cost-effectively, for example, in the casting method or in the 3D printing method.

In a further advantageous refinement of the invention, the spacer elements are embedded in the interior of the projections, in particular embedded completely in the interior of the projections, in order to reinforce the projections. In this case, the projections of the structure are thus only partially formed by the spacer elements. In this case, the spacer elements act as reinforcements of the projections and in particular enhance the rigidity of the projections. The spacer elements can in particular be completely embedded, i.e., enclosed on all sides.

Such an embodiment offers the advantage that the contact surface of the electrode arrangement on the surface to be treated is not necessarily formed by the spacer elements. The structure can be manufactured in this case from a material having particularly high flexibility, in particular particularly low hardness, in which the spacer elements, which are manufactured from a material of lesser flexibility, in particular greater hardness, are embedded. The contact surface on the surface to be treated is thus formed by the more flexible material of the structure. On the one hand, a stronger hold of the electrode arrangement on the surface to be treated and a particularly good adaptation of the shape of the electrode arrangement to the surface to be treated can thus advantageously be achieved. On the other hand, the electrode arrangement can thus advantageously be perceived as particularly pleasant on the surface of a human or animal body.

In a further advantageous refinement of the invention, it is provided that the projections of the structure are formed from the spacer elements and the dielectric material, wherein the spacer elements are embedded, in particular completely embedded, in the dielectric material enclosing the spacer elements.

In this embodiment, the spacer elements are thus at least partially, preferably completely, embedded in the dielectric material, which at least partially, preferably completely, encloses the spacer elements. Since the material of the dielectric material has a greater flexibility according to the invention than the material of the spacer elements, the advantages mentioned in conjunction with the above-described advantageous refinement can be implemented in a particularly simple manner using this embodiment.

In this case, the part of the structure enclosing the spacer elements, in particular the part of the dielectric material enclosing the spacer elements, can advantageously be formed for a contact on the skin of a living being.

In a further advantageous refinement of the invention, it is provided that the dielectric material enclosing the spacer elements is integrally formed with the layer of the dielectric material preventing the direct current flow.

It is thus proposed that the dielectric material enclosing the spacer elements and the layer of the dielectric material preventing the direct current flow are integrally manufactured. In particular the entire dielectric material including the part of the dielectric material enclosing the spacer elements can advantageously be integrally formed, i.e., integrally manufactured.

These embodiments of the electrode arrangement according to the invention offer the advantage that the electrode arrangement is producible particularly simply and cost-effectively in the casting method. In this case, the spacer elements can be embedded easily into the dielectric material. However, the rapid buildup in the manner of a prototype in the 3D printing method is also advantageously possible.

Alternatively, however, it is also conceivable that the part of the structure enclosing the spacer elements, in particular the part of the dielectric material enclosing the spacer elements, is formed as a separate part, to then be attached on the layer of the dielectric material preventing the direct current flow. The production of a permanent connection can be performed in a typical manner, i.e., mechanically in a housing structure, in a formfitting and/or materially-bonded manner, in particular by adhesive bonding or welding. It is also possible here that the spacer elements are embedded into the structure.

Such a form of a separately produced structure offers the advantage that in particular during the cleaning of wounds, easy replaceability of the part of the electrode arrangement coming into contact with the wound can be enabled. For this purpose, the separate structure including the spacer elements can be used as a removable single-use part or also can be easily sterilized because of its small volume.

The spacer elements as such can advantageously also be manufactured in a corresponding manner in the casting method or in the 3D printing method.

In a further advantageous refinement of the invention, it is provided that the projections of the structure are completely formed by the spacer elements. In this case, the spacer elements are connected on the side thereof facing toward the electrode to the layer preventing a direct current flow and form a contact surface on the surface to be treated on the side thereof facing toward the surface to be treated.

In this embodiment, the projections of the structure are thus formed solely by the spacer elements. The spacer elements are accordingly not embedded in the projections, but rather themselves form the projections and for this purpose are joined on the side facing away from the surface to be treated to the layer preventing a direct current flow, i.e., connected thereto. The production of a permanent connection between the spacer elements and the layer of the dielectric material can again be performed in a typical manner in this case, i.e., mechanically in a housing structure, in a formfitting and/or materially-bonded manner, in particular by adhesive bonding or welding. On the side facing away from the electrode, i.e., on the side of the spacer elements facing toward the surface to be treated, the spacer elements form a contact surface on the surface to be treated. In this embodiment, the spacer elements thus rest on the surface to be treated during the treatment.

Such an embodiment offers the advantage that the electrode arrangement can be produced particularly simply, since the spacer elements, after the production thereof, for example, in the casting method or in the 3D printing method, solely have to be joined to the dielectric material.

The connection between the spacer elements and the layer of the dielectric material preventing a direct current flow can advantageously in particular be a detachable connection. This offers the advantage that in particular during the treatment of wounds, an easy replaceability of the spacer elements coming into contact with the wound is enabled, which again can be used as removable single-use parts or can be easily sterilized because of the small volume thereof.

The spacer elements can advantageously be configured for a contact on the skin of a living being.

In a further advantageous refinement of the invention, it is provided that the structure is a grid structure made of adjoining walls forming the projections, which delimit numerous chambers forming the air spaces. The grid structure can advantageously be formed in particular integrally with the layer of the dielectric material preventing the direct current flow. Alternatively, however, the grid structure can also be manufactured as a separate part and attached to the layer of the dielectric material preventing the direct current flow.

The spacer elements can advantageously be embedded in the walls of the grid structure in this case, in particular completely embedded in the walls of the grid structure.

Such a grid structure known from DE 10 2015 117 715 A1, which was mentioned at the outset, offers the advantages in combination with the spacer elements of the electrode arrangement according to the invention that it can be made particularly flexible and light and at the same time, due to the spacer elements according to the invention, reliably ensures the distance is maintained between the surface to be treated and the layer preventing the direct current flow—and thus the effective formation of the plasma.

In a further advantageous refinement of the invention, it is provided that the structure consists of protruding nubs forming the projections, which form the air spaces in the intermediate spaces thereof. The spacer elements can advantageously be embedded in the nubs in this case, in particular completely embedded in the nubs.

The nubs can advantageously be formed circular-cylindrical, conical, or in the form of a truncated cone.

Such embodiments, in which the structure consists of protruding nubs, offer the advantages that they may be manufactured simply and cost-effectively and adapt well to the surface to be treated if a sufficiently flexible material is used, wherein the sufficient formation of the air spaces required for the plasma formation can be ensured by the spacer elements according to the invention.

In a further advantageous refinement of the invention, it is provided that the projections of the structure are formed completely by the spacer elements in the above-described manner and the spacer elements have the form of protruding nubs, which form the air spaces in the intermediate spaces thereof. The nubs can again advantageously be formed circular-cylindrical, conical, or in the form of a truncated cone.

This refinement of the electrode arrangement according to the invention is thus similar to the above-described refinement, wherein the spacer elements themselves have the form of protruding nubs, however. Accordingly, the nubs are manufactured from the second material, the flexibility of which is less than the flexibility of the first material, from which the dielectric material of the electrode arrangement is manufactured.

Such an embodiment, in which the spacer elements have the form of protruding nubs, offers the advantage that they may be produced particularly simply and cost-effectively. For this purpose, the structure having the spacer elements forming the projections in the form of protruding nubs can be formed in particular in one piece, so that particularly simple and cost-effective manufacturing is possible, for example, in the casting method or in the 3D printing method.

In a further advantageous refinement of the invention, it is provided that the spacer elements are each formed from a circumferential wall.

The wall extends around the spacer element on the sides of the spacer element which are not the side of the spacer element facing toward the surface to be treated and are not the side of the spacer element facing toward the layer preventing a direct current flow. The circumferential wall forms the lateral delimitation of an interior space enclosed thereby in this manner. The circumferential wall, from which the respective spacer element is formed, can consist of a single circumferential wall or of multiple adjoining walls. The height of the spacer elements is defined by the height of the circumferential wall.

In a further advantageous refinement of the invention, it is provided that the circumferential walls of the spacer elements each enclose an air space.

The spacer elements can accordingly be arranged in the electrode arrangement in such a way that the air spaces for the formation of the plasma are formed within the interior space delimited by the circumferential wall of the respective spacer element.

The circumferential walls of the spacer elements can advantageously each have a quadrilateral, in particular rectangular or square, cross section. The circumferential walls of the spacer element can advantageously also have a round or oval cross section, however. The circumferential walls of the spacer elements can advantageously also have a polygonal, in particular a honeycomb-shaped cross section, however.

The material thickness of the wall can advantageously make up less than 20%, in particular less than 10%, of the greatest width of the space enclosed by the wall. The material thickness of the wall can advantageously be, for example, between 0.1 mm and 1.0 mm.

Such embodiments of the electrode arrangement according to the invention having spacer elements which are each formed from a circumferential wall offer the advantage according to the invention that the spacer elements have a particularly high level of stability because of the shape thereof. The spacer elements can thus be manufactured with low material expenditure. Moreover, they have a particularly small cross-sectional area. In this way, the projections of the structure in turn advantageously only occupy a small area on the surface to be treated and a larger part of the surface to be treated is available for the formation of the air spaces and thus for the formation of the plasma. A particularly effective plasma treatment is thus advantageously possible.

In a further advantageous refinement of the invention, it is provided that the spacer elements and/or the projections of the structure have a uniform height.

A particularly uniform formation of the plasma can thus advantageously be achieved. In addition, it is possible in this manner that chambers are formed between the projections, which are laterally closed and form a self-contained air space when the electrode arrangement rests on the surface to be treated. Experiments have shown that a suitable plasma can also be formed in such self-contained chambers.

The invention is to be explained in greater detail hereafter on the basis of the exemplary embodiments schematically illustrated in the appended drawings. In the figures:

FIG. 1a)—shows a view of an upper side of a first embodiment of an electrode arrangement;

FIG. 1b)—shows a vertical section along line A-A in FIG. 1a);

FIG. 1c)—shows a detail view of the detail A in FIG. 1b);

FIG. 2a)—shows a view of a contact side of the first embodiment of an electrode arrangement;

FIG. 2b)—shows a vertical section along line B-B in FIG. 2a);

FIG. 3a)—shows a horizontal section along line C-C in FIG. 1b);

FIG. 3b)—shows a horizontal section along line D-D in FIG. 1b);

FIG. 4a)—shows a view of an upper side of a second embodiment of an electrode arrangement;

FIG. 4b)—shows a vertical section along line A-A in FIG. 4a);

FIG. 4c)—shows a detail view of the detail A in FIG. 4b);

FIG. 5a)—shows a view of a contact side of the second embodiment of an electrode arrangement;

FIG. 5b)—shows a vertical section along line B-B in FIG. 5a);

FIG. 6a)—shows a horizontal section along line C-C in FIG. 4b);

FIG. 6b)—shows a horizontal section along line D-D in FIG. 4b);

FIG. 7a)—shows a view of an upper side of a third embodiment of an electrode arrangement;

FIG. 7b)—shows a vertical section along line A-A in FIG. 7a);

FIG. 7c)—shows a detail view of the detail A in FIG. 7b);

FIG. 8a)—shows a view of a contact side of the third embodiment of an electrode arrangement;

FIG. 8b)—shows a vertical section along line B-B in FIG. 8a).

The exemplary embodiment illustrated in FIG. 1a) shows an upper side 8, i.e., a side facing away from the surface to be treated, of a first exemplary embodiment of an electrode arrangement for a dielectric barrier plasma treatment of a surface of a body. The upper side 8 of a dielectric material 2 having an essentially square cross section can be seen. On one side, the electrode arrangement extends in a web-shaped attachment 10. The dielectric material 2 comprises a plurality of through openings 11, which enable, for example, the discharge of a fluid, in particular a liquid, from the surface to be treated. The electrode arrangement additionally comprises multiple wing-shaped sections 12, which are particularly flexible having a low thickness and are formed adhesive on the lower side thereof, in order to enable the fastening of the electrode arrangement on the skin of a living being, possibly around a wound.

The dielectric material 2 is manufactured from a particularly flexible silicone, which has a low hardness of only 20 Shore. The dielectric material 2 thus only has a very low rigidity but can adapt its shape very well to the surface to be treated.

FIG. 1b) shows a vertical section through the electrode arrangement along line A-A in FIG. 1a). Details can be inferred from the detail view of the detail A in FIG. 1c). A flexible planar electrode 1, which is enclosed on all sides by the dielectric material 2, can be seen. The dielectric material 2 forms in particular a layer 3 preventing a direct or galvanic current flow, which extends along the entire surface of the electrode 1 and thus shields the electrode completely from the surface to be treated. A direct or galvanic current flow from the electrode 1 to the surface to be treated is thus prevented.

The dielectric material 2 can rest via a structure 4 having projections 7 on the surface to be treated and forms air spaces 5 for the formation of the plasma between the projections 7. The air spaces 5 have a bottom-side termination by the layer 3 of the dielectric material 2 preventing the direct current flow and a side open toward the surface to be treated and are thus open on a contact side 9 of the electrode arrangement.

It can furthermore be seen that not only the dielectric material 2 comprises through openings 11, but rather the electrode 1 also comprises through openings 13. The through openings 11 of the dielectric material are aligned with the through openings 13 of the electrode and the air spaces 5 between the projections 7 of the structure 4, so that the discharge of a fluid, in particular a liquid, from the surface to be treated is possible through the through openings 11, 13.

Furthermore, it may be seen from FIGS. 1b) and 1c) that the structure 4 comprises a plurality of spacer elements 6, which are manufactured in this exemplary embodiment from a stable plastic. The flexibility of this stable plastic is less than the flexibility of the silicone, from which the dielectric material 2 is manufactured.

The spacer elements 6 are each formed in this exemplary embodiment from a circumferential wall, which encloses an air space 5 in each case. The circumferential walls of the spacer elements 6 have a rectangular cross section.

Moreover, it may be seen from FIGS. 1b) and 1c) that the projections 7 of the structure 4 are partially formed by the spacer elements 6, namely from the spacer elements 6 and the dielectric material 2. The spacer elements 6 are completely embedded into the dielectric material 2 enclosing them and thus form a reinforcement of the projections 7. The dielectric material 2 enclosing the spacer elements 6 is integrally formed with the layer 3 of the dielectric material 2 preventing the direct current flow. This enables a particularly simple and cost-effective manufacturing of the dielectric material 2 in the casting method, wherein the spacer elements 6 are embedded in the dielectric material 2.

The spacer elements 6 are connected to one another via connecting sections 18, which have a lower bending rigidity and a lower torsional rigidity than the spacer elements 6. The connecting sections 18 between the spacer elements 6 are formed by the dielectric material 2, namely by the layer 3 of the dielectric material 2 preventing a direct current flow. Since the particularly flexible silicone of the dielectric material 2 has a greater flexibility than the stable plastic of the spacer elements 6, the connecting sections 18 can have a lower bending and torsional rigidity than the spacer elements 6 particularly simply in this way. The structure 4 thus has a significantly higher flexibility in the area than in the height.

The electrode arrangement rests during the treatment with the very soft and flexible dielectric material 2 on the skin surface to be treated Both the spacer elements 6 and also the projections 7 of the structure 4 have a uniform height in this exemplary embodiment.

Moreover, it is clear that the electrode 1 extends into the web-shaped attachment 10. The dielectric material 2 has openings 15 in the region of the web-shaped attachment 10, via which the contacting of the electrode 1 can be performed to supply a high voltage required for the plasma generation, which is preferably used as an AC voltage.

FIG. 2*a*) shows the contact side 9 of the electrode arrangement of the first exemplary embodiment. It can be seen in particular that the structure 4 is formed as a grid structure made of walls adjoining one another, which form the projections 7, wherein the walls delimit numerous chambers 17 forming the air spaces 5. The walls of the grid structure here form, on the side thereof facing toward the surface to be treated, a contact surface on the surface to be treated.

The web-shaped attachment 10 comprises two openings 15 for the contacting in each case of one electrode 1 of the electrode arrangement, since the electrode arrangement comprises a total of two electrodes 1, as will be clear hereafter.

FIG. 2*b*) shows a vertical section through the electrode arrangement along line B-B in FIG. 2*a*). It can be seen that the electrode arrangement comprises two electrodes 1, which are enclosed on all sides by the dielectric material 2. The dielectric material 2 therefore comprises a middle region 16 in which the electrodes 1 do not extend.

The spacer elements 6 are embedded in the walls formed from the dielectric material 2, which form the projections 7.

Otherwise, the above statements on FIGS. 1*a*) to 1*c*) can be made with respect to FIGS. 2*a*) and 2*b*).

FIG. 3*a*) shows a horizontal section through the electrode arrangement of the first exemplary embodiment along line C-C in FIG. 1*b*). It can be seen that the structure 4 comprises a plurality of spacer elements 6, which form the projections 7 together with the dielectric material 2. The spacer elements 6 are each formed from a circumferential wall and each enclose an air space 5, which is formed in a chamber 17, which is delimited by the walls of the grid structure 4. The wall of the spacer elements 6 accordingly encloses the chamber 17 formed by the walls of the grid structure 4.

It can be seen clearly that each spacer element 6 respectively has a quadrilateral cross section.

FIG. 3*b*) shows a horizontal section through the electrode arrangement of the first exemplary embodiment along line D-D of FIG. 1*b*). It is recognizable that the electrode arrangement comprises two electrodes 1 and a middle region 16 of the dielectric material 2, in which the electrodes 1 do not extend. The electrodes 1 each extend in the web-shaped attachment 10 in order to enable the contacting thereof.

It can also be seen that the through openings 11 of the dielectric material 2 have a smaller diameter than the through openings 13 of the electrode 1. It can thus be ensured that the dielectric material 2 encloses the electrode 1 on all sides and thus shields the electrode 1 completely from the surface to be treated. The fact that the dielectric material 2 extends on its lateral edges beyond the area of the electrode 1 is used for the same purpose, so that the electrode 1 is also completely enclosed by the dielectric material 2 at the lateral edges of the electrode arrangement.

Otherwise, reference can be made to the statements on FIGS. 1 and 2 with respect to FIGS. 3*a*) and 3*b*).

Figure 3:
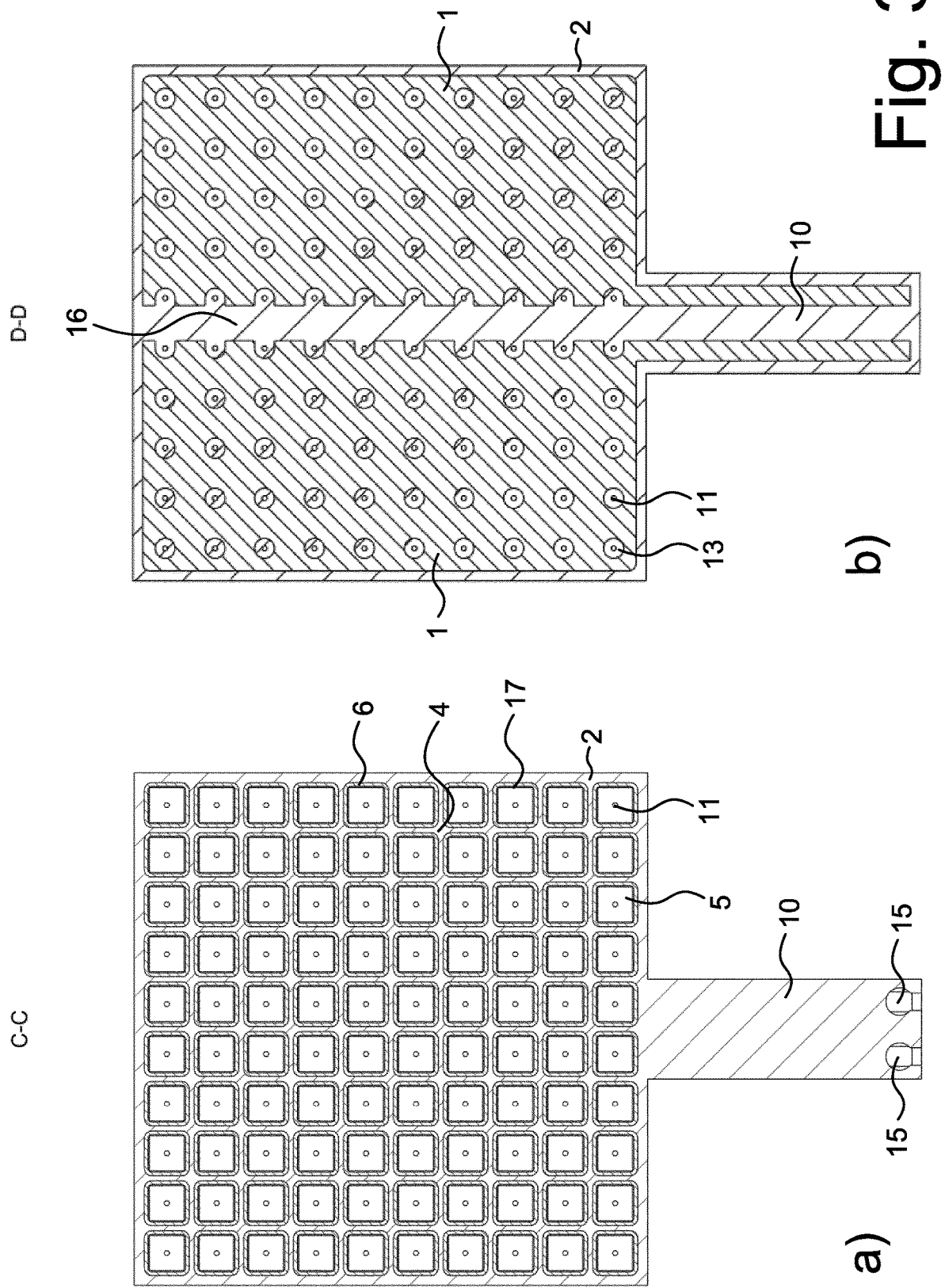
Figure 4:
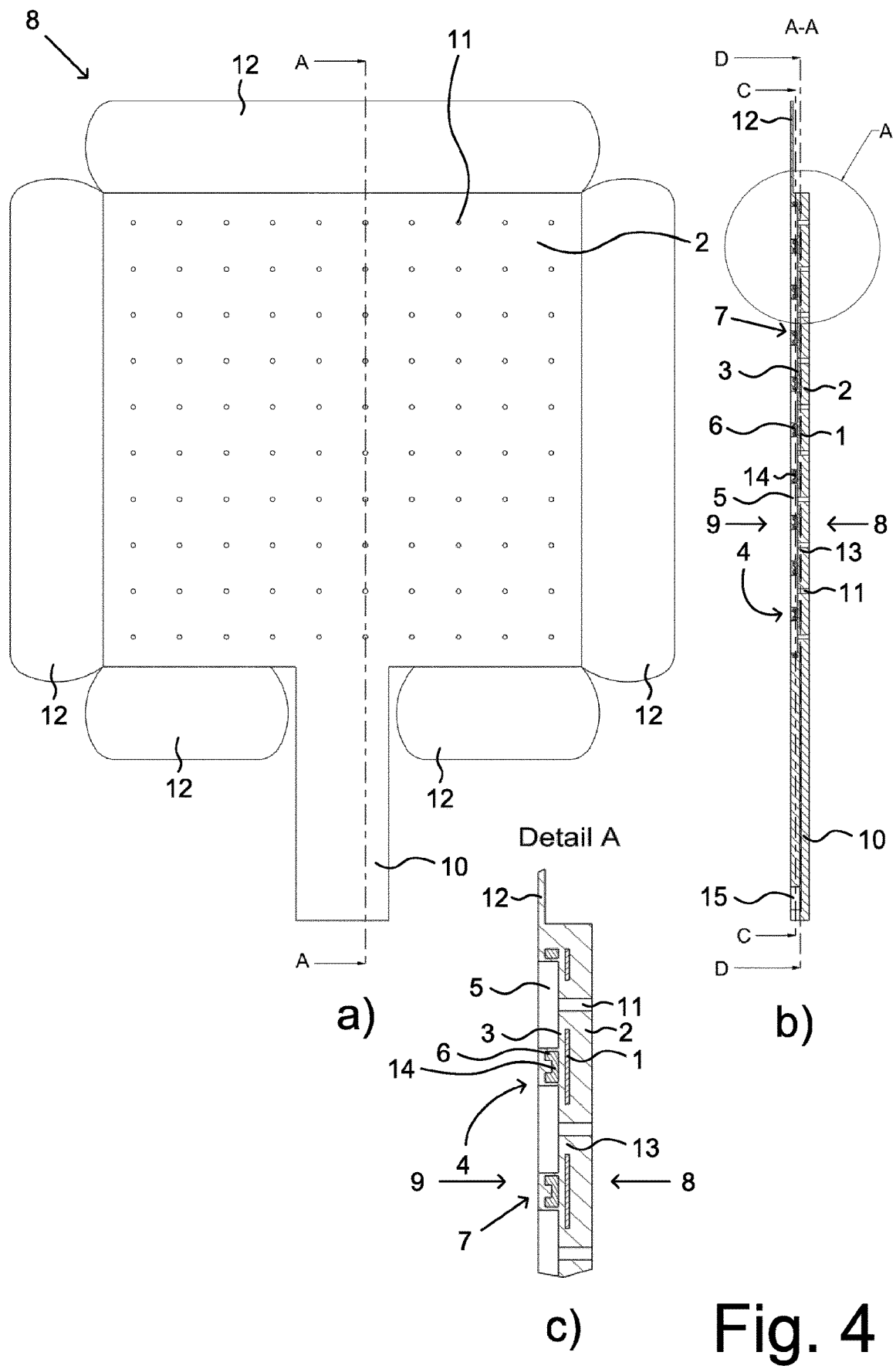
Figure 6:
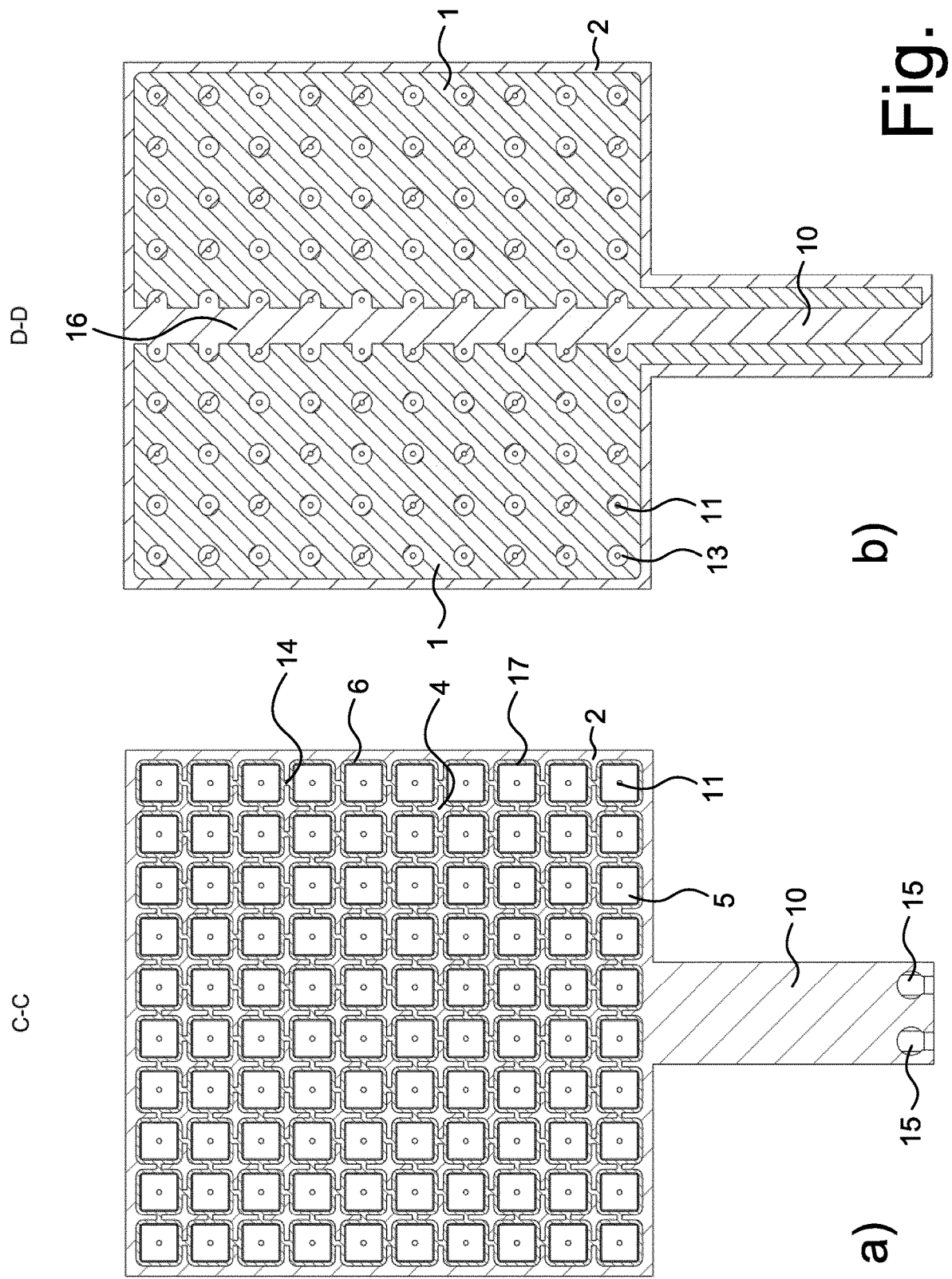

FIGS. 4, 5, and 6 show a second exemplary embodiment of an electrode arrangement according to the invention in a form of illustration corresponding to FIGS. 1, 2, and 3, respectively.

This second exemplary embodiment of the electrode arrangement according to the invention differs, as can be seen in particular in FIGS. 4*b*), 4*c*), 5*b*), and 6*a*), from the first exemplary embodiment in that the spacer elements 6 are connected to one another by connecting webs 14. The spacer elements 6 form a spacer grid in this manner. A particularly high level of stability of the spacer elements 6 can thus be achieved, which ensures particularly reliably that the required distance between the surface to be treated and the layer 3 preventing a direct current flow is maintained during the treatment.

The spacer grid formed from the spacer elements 6 with the aid of the connecting webs 14 is integrally formed in this exemplary embodiment and therefore can be manufactured particularly simply in the casting method.

Otherwise, reference can be made to the statements on the first exemplary embodiment with respect to the second exemplary embodiment shown in FIGS. 4 to 6.

Figure 7:
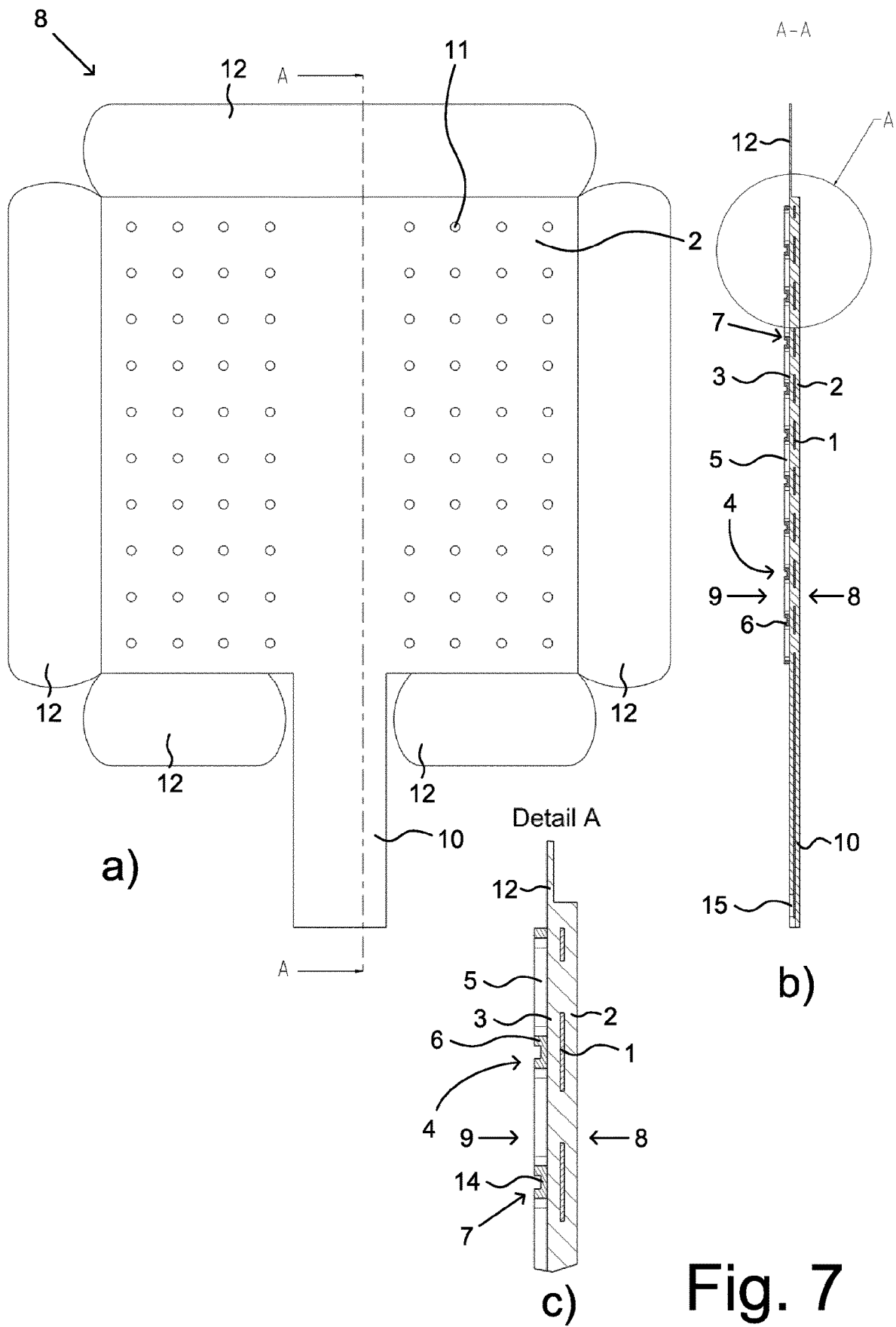

FIGS. 7 and 8 show a third exemplary embodiment of an electrode arrangement according to the invention in a form of illustration corresponding to FIGS. 1 and 2 and FIGS. 4 and 5, respectively.

This third exemplary embodiment of the electrode arrangement according to the invention differs, as can be seen in FIGS. 7*b*), 7*c*), 8*a*), and 8*b*), from the first and second exemplary embodiment in that the projections 7 of the structure 4 are formed solely by the spacer elements 6. The spacer elements 6 are connected on the side thereof facing toward the electrode 1 to the layer 3 of the dielectric material 2 preventing a direct current flow. On the opposite side of the spacer elements 6, which faces toward the surface to be treated, the spacer elements 6 form a contact surface on the surface to be treated. The spacer elements 6 have a uniform height, are formed for contact on the skin of a living being, and rest on the skin during the treatment.

In contrast to the first and second exemplary embodiment, the spacer elements 6 in the third exemplary embodiment shown in FIGS. 7 and 8 are thus not embedded in the projections 7, but rather the spacer elements 6 themselves form the complete projections 7. For this purpose, the spacer elements 6 and the layer 3 of the dielectric material 2 preventing a direct current flow are joined to one another by adhesive bonding, i.e., permanently connected to one another by a materially-bonded connection.

The spacer elements 6 are each formed from a circumferential wall, which has an essentially square cross section and encloses an air space 5. In addition, in contrast to the first and second exemplary embodiment, in this third exemplary embodiment, air spaces 5, in which the plasma can form, are also provided in the intermediate spaces between the various spacer elements 6.

In accordance with the second exemplary embodiment, the spacer elements 6 are also connected to one another by connecting webs 14 in the third exemplary embodiment. The spacer elements 6 form an integrally embodied spacer grid in this manner, which can be manufactured particularly simply in the casting method.

Otherwise, reference can be made to the statements on the first and second exemplary embodiment with respect to the third exemplary embodiment shown in FIGS. 7 and 8.

The invention claimed is:

1. An electrode arrangement for a dielectric barrier plasma treatment of a surface of a body, comprising:

at least one flexible planar electrode;
a dielectric material made of a planar flexible first material which includes a layer that shields the at least one flexible planar electrode from the surface of the body to be treated and prevents a direct current flow,
   wherein the dielectric material is configured to rest on the surface of the body to be treated via a structure having projections,
   wherein air spaces for formation of a plasma are between the projections,
wherein the structure comprises
   a side open toward the surface of the body to be treated,
   a bottom-side termination by the layer of the dielectric material which prevents the direct current flow, and
   a plurality of spacer elements made of a second material, wherein a flexibility of the second material is less than the flexibility of the first material, wherein the projections of the structure are partially or completely formed by the spacer elements.

2. The electrode arrangement as claimed in claim 1, wherein the spacer elements are connected to one another via connecting sections which have a lower bending rigidity and/or a lower torsional rigidity than the spacer elements.

3. The electrode arrangement as claimed in claim 1 wherein the spacer elements are connected to one another by connecting webs, wherein the spacer elements and the connecting webs form a spacer grid.

4. The electrode arrangement as claimed in claim 3, wherein the spacer grid is integrally formed.

5. The electrode arrangement as claimed in claim 1 wherein the spacer elements are embedded in an interior of each of the projections so as to reinforce the projections.

6. The electrode arrangement as claimed in claim 1 wherein the projections of the structure are formed from the spacer elements and the dielectric material, wherein the spacer elements are embedded in the dielectric material and the dielectric material encloses the spacer elements.

7. The electrode arrangement as claimed in claim 6, wherein the dielectric material that encloses the spacer elements is integrally formed with the layer of the dielectric material that prevents the direct current flow.

8. The electrode arrangement as claimed in claim 1 wherein the projections of the structure are completely formed by the spacer elements, wherein the spacer elements are connected on a side of the structure facing toward the electrode to the layer of the dielectric material that prevents a direct current flow, and wherein the spacer elements form a contact surface on the surface of the body to be treated on the side of the structure facing toward the surface of the body to be treated.

9. The electrode arrangement as claimed in claim 1 wherein the structure is a grid structure made of adjoining walls forming the projections, which delimit numerous chambers that form forming the air spaces.

10. The electrode arrangement as claimed in claim 1 wherein the structure comprises protruding nubs that form the projections.

11. The electrode arrangement as claimed in claim 8, wherein the spacer elements have the form of protruding nubs.

12. The electrode arrangement as claimed in claim 10 wherein the protruding nubs are in a form of a circular-cylindrical, conical, or truncated cone.

13. The electrode arrangement as claimed in claim 1 wherein the spacer elements are each formed from a circumferential wall.

14. The electrode arrangement as claimed in claim 13, wherein the circumferential walls of the spacer elements each enclose an air space.

15. The electrode arrangement as claimed in claim 13 wherein the circumferential walls each have a quadrilateral, round, oval, or polygonal cross section.

16. The electrode arrangement as claimed in claim 1 wherein the spacer elements and/or the projections of the structure have a uniform height.

* * * * *